United States Patent
O'Donnell et al.

(10) Patent No.: US 10,722,229 B2
(45) Date of Patent: Jul. 28, 2020

(54) SUTURE CRIMP PLATE

(71) Applicant: DePuy Synthes Products, Inc., Raynham, MA (US)

(72) Inventors: Thomas O'Donnell, Philadelphia, PA (US); Robert Limouze, East Fallowfield, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 128 days.

(21) Appl. No.: 16/049,738

(22) Filed: Jul. 30, 2018

(65) Prior Publication Data

US 2020/0029957 A1     Jan. 30, 2020

(51) Int. Cl.
*A61B 17/04* (2006.01)

(52) U.S. Cl.
CPC ...... *A61B 17/0487* (2013.01); *A61B 17/0401* (2013.01); *A61B 2017/0454* (2013.01)

(58) Field of Classification Search
CPC ...... A61B 2017/0459; A61B 2017/042; A61B 2017/0422; A61B 2017/0424; A61B 2017/0425; A61B 2017/0487; A61B 17/0401; A61B 2017/0404; A61B 2017/0406; A61B 2017/0414; A61B 2017/0446

See application file for complete search history.

(56) References Cited

U.S. PATENT DOCUMENTS

| | | | |
|---|---|---|---|
| 6,093,201 A | 7/2000 | Cooper et al. | |
| 6,520,965 B2 | 2/2003 | Chervitz et al. | |
| 6,533,816 B2 | 3/2003 | Sklar et al. | |
| 7,491,217 B1 | 2/2009 | Hendren et al. | |
| 7,833,244 B2 | 11/2010 | Cerundolo | |
| 7,862,584 B2 * | 1/2011 | Lyons | A61B 17/0487 606/232 |
| 8,142,434 B2 | 3/2012 | Bluechel | |
| 8,444,674 B2 | 5/2013 | Kaplan | |
| 2006/0190041 A1 * | 8/2006 | Fallin | A61B 17/0401 606/232 |
| 2011/0202002 A1 * | 8/2011 | Gordon | A61B 17/0401 604/103.13 |
| 2013/0110164 A1 * | 5/2013 | Milazzo | A61B 17/0487 606/232 |
| 2014/0031864 A1 * | 1/2014 | Jafari | A61B 17/0487 606/232 |

(Continued)

*Primary Examiner* — Wade Miles
(74) *Attorney, Agent, or Firm* — Fay Kaplun & Marcin, LLP

(57) ABSTRACT

A suture crimp plate includes a body including a first bone-facing surface and a second opposing surface; a central hole extending through the body from the first surface to the second surface and sized and shaped to receive a bone fixation device; and a first suture hole extending through the body from the first surface to the second surface and sized and shaped to receive a suture therethrough. The first suture hole is open to the central hole via a first slot, a first deformable member being formed between the first suture hole and the central hole. When a bone fixation element is inserted into the central hole, the first deformable member is configured to be deflected away from a central longitudinal axis of the central hole and into the first suture hole to clamp the suture therein relative to the crimp plate.

20 Claims, 2 Drawing Sheets

(56) References Cited

U.S. PATENT DOCUMENTS

| | | |
|---|---|---|
| 2015/0164498 A1 | 6/2015 | Dreyfuss et al. |
| 2016/0089131 A1 | 3/2016 | Wade |
| 2016/0270776 A1* | 9/2016 | Miraki ............... A61B 17/0487 |

* cited by examiner

SUTURE CRIMP PLATE

FIELD

The present invention relates to the field of surgery and, more particularly, to methods of incorporating suture or similar materials in orthopedic procedures.

BACKGROUND

Fixation devices such as screws are often used in orthopedic procedures to stabilize the bone and facilitate tissue healing. Often, it is necessary to incorporate sutures in these orthopedic repairs for additional fixation. However, existing suture fixation devices for some procedures such as, for example, ankle syndesmosis can have a large knot stack after tying, causing soft tissue irritation. Knots may also slip and relax over time requiring additional operations.

SUMMARY

The present disclosure relates to a suture crimp plate comprising a body including a first bone-facing surface and a second opposing surface, a central hole extending through the body from the first surface to the second surface and sized and shaped to receive a bone fixation device, a first suture hole extending through the body from the first surface to the second surface and sized and shaped to receive a suture therethrough, the first suture hole being open to the central hole via a first slot, a first deformable member being formed between the first suture hole and the central hole. When a bone fixation element is inserted into the central hole, the first deformable member is configured to be deflected away from a central longitudinal axis of the central hole and into the first suture hole to clamp the suture therein relative to the crimp plate.

The present disclosure also relates to an implant system including a crimp plate which has a body including a first bone-facing surface and a second opposing surface; a central hole extending through the body from the first surface to the second surface and sized and shaped to receive a bone fixation device; and a first suture hole extending through the body from the first surface to the second surface and sized and shaped to receive a suture therethrough, the first suture hole being open to the central hole via a first slot, a first deformable member being formed between the first suture hole and the central hole. The system also includes a bone fixation element configured to be inserted through the central hole such that, when the bone fixation element is inserted through the central hole, the first deformable member is deflected away from a central longitudinal axis of the central hole and into the first suture hole to clamp the suture therein relative to the crimp plate; and at least one suture configured to be passed through the first suture hole.

BRIEF DESCRIPTION

DETAILED DESCRIPTION

Figure 1:
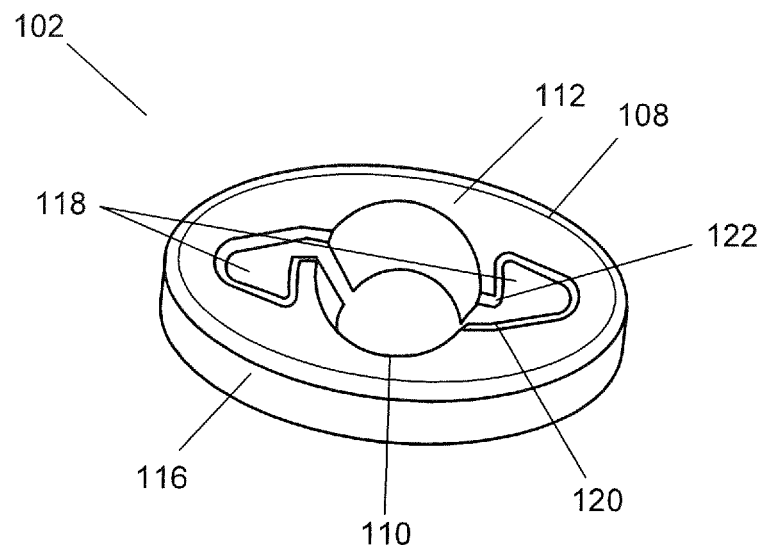
FIG. 1 shows a perspective view of a crimp plate according to an exemplary embodiment of the present disclosure.

The exemplary embodiments may be further understood with reference to the following description and the related appended drawings, wherein like elements are provided with the same reference numerals. The present disclosure relates to an implant system including a suture fixation device used for ankle syndesmosis repair. Specifically, the present disclosure relates to a crimp plate that is capable of tensioning a suture using a fixation device to reduce a syndesmosis without requiring suture knots. It should be noted that the terms "proximal" and "distal," as used herein, are intended to refer to a direction toward (proximal) and away from (distal) a user of the system (e.g., a physician).

Figure 2:
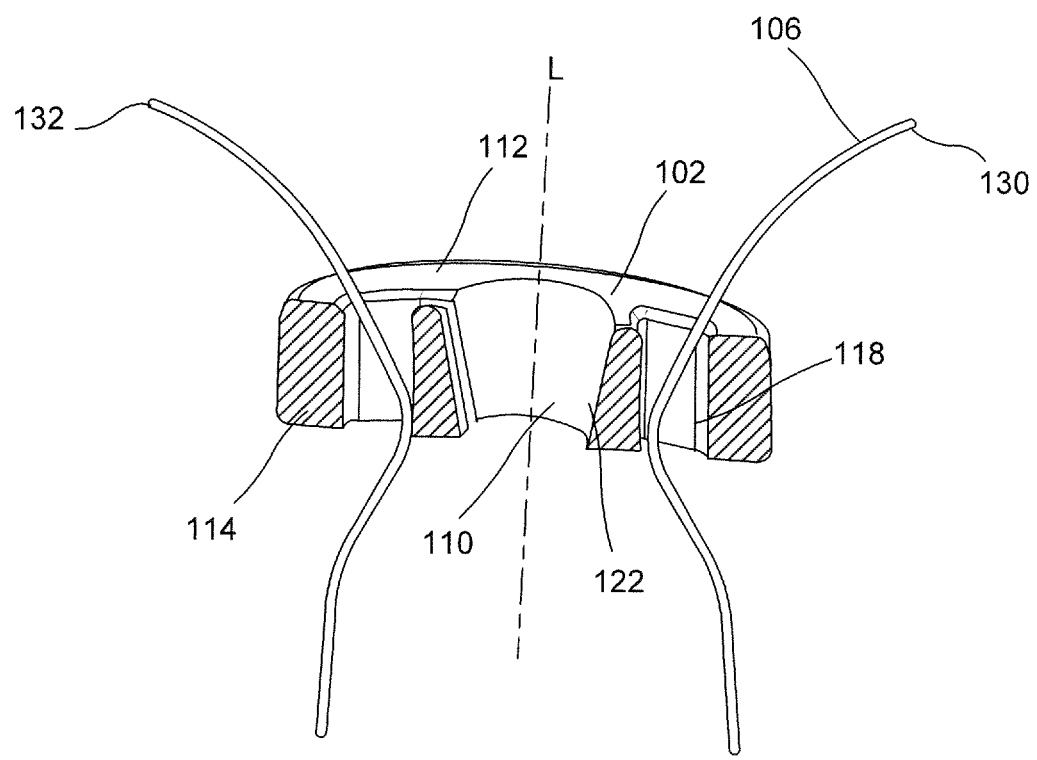
FIG. 2 shows a cross-sectional view of the crimp plate of FIG. 1.
Figure 3:
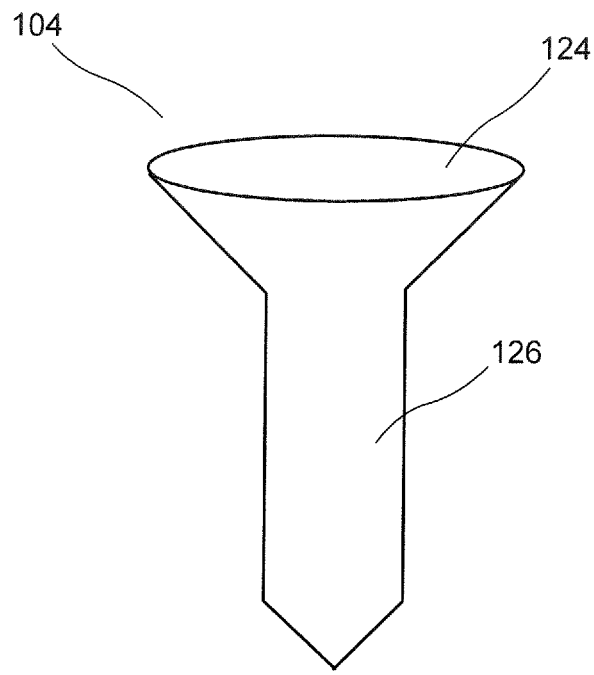
FIG. 3 shows a perspective view of a locking screw according to an exemplary embodiment of the present disclosure.

Looking to FIGS. 1-3, an implant system 100 includes a crimp plate or washer 102, a fixation device 104 configured to be inserted through the crimp plate 102 and at least one suture 106. The crimp plate 102 is designed to be flexibly secured to tissue (for example, bone) by means of the fixation device 104. The crimp plate 102 has a substantially disc-shaped body 108 that defines a central hole 110. The crimp plate preferably has a planar first surface 112, a parallel planar second surface 114, and a perimeter surface 116 extending therebetween. The central hole 110 extends from the first surface 112 to the second surface 114 and is sized and shaped to receive the fixation device 104. The central hole 110, in this embodiment, is a 3.5 mm screw hole that may, for example, be a locking hole. However, it will be understood by those skilled in the art that the central hole 110 may be any size depending on the procedure and application so long as it fits the locking device to be used therewith. The central hole 110 tapers in diameter from the first surface 112 to the second surface 114. Although FIGS. 1-2, show a smooth inner surface for the central hole 110, those skilled in the art will understand that the central hole 110 may include threading on an inner surface thereof configured to mate with threading on an outer surface of the locking screw 104. As can be seen in FIG. 1, the crimp plate 102 also includes two suture holes or passages 118. It is understood that although the crimp plate 102 of the present embodiment is depicted with two suture holes 118, any number of suture holes 110 may be used depending on the procedure, as will be described in further detail below.

The suture holes 118 extend from the first surface 112 to the second surface 114 and are separated from one another on opposing sides of the central hole 110, as shown in FIG. 1. As would be understood by those skilled in the art, because the suture holes 118 are positioned on the outside of the central hole 110, the suture 106 will naturally be pulled towards the outer edges of the crimp plate 102 when tension is applied thereto. In the current embodiment, the suture holes 118 have a substantially triangular profile in a plane perpendicular to a longitudinal axis of each of the suture hole 118. However, the profile of the suture holes 118 may take any shape such as, for example, rectangular, oval, circular, etc. A slot 120 extends from each suture hole 118 to the central hole 110 such that the suture holes 118 are open to the central hole 110. The slots 120 extend from the first surface 112 to the second surface 114 to facilitate deformation of the deformable members 122 extending between the central hole 110 and a portion of the perimeter of each suture hole 118. In a preferred embodiment, the slots 120 have a width smaller than the width of the suture 106 to prevent the suture 106 from passing therethrough into the central hole 110. The deformable members 122 are movable radially outward from a central longitudinal axis L of the crimp plate 102 into the suture holes 118. This deflection of the deformable members 122 into the suture holes 118 clamps the suture 106 into place, as will be described in further detail below.

The crimp plate 102 may be formed of metal such as, for example, stainless steel, titanium, titanium alloy, or other biocompatible metals or compositions. In an exemplary embodiment, the deformable members 122 may be formed of nitinol or another shape-memory material so that the deformable members 122 may be deflected and released multiple times without permanently deforming the deformable members 122. This shape-memory of the deformable members 122 allows for the suture 106 to be fully locked and unlocked by advancing and reversing the locking screw 106. However, those skilled in the art will understand that other materials with conventional spring properties may also be used.

As shown in FIG. 3, the fixation element 104, in this embodiment, may be any bone screw including a head 124 and a shaft 126 configured to be inserted into bone such as, for example, a locking screw with a threaded head configured to mate with corresponding threading in a locking screw hole. In an exemplary embodiment, the fixation element 104 is a standard 3.5 mm locking screw sufficient to withstand the loads applied when tensioning the crimp plate 102 and to endure subsequent stresses after implantation on target tissue. However, it will be understood that the fixation element 104 may be any size, depending on the location of the system and the procedure. The fixation element 104 preferably has a flat head 124 to allow the fixation element 104 to lie flush with the crimp plate 102 when inserted therein and into the target tissue. The length of the shaft 126 is sufficient to withstand the required loads and provide adjustment of the suture 106 and crimp plate 102 during implantation on or within target tissue. In an exemplary embodiment, the fixation element 104 may include threading along the outside of the shaft 126 and the head 124 to promote locking of the fixation element within the target tissue and the crimp plate 102. In another embodiment, the shaft 126 may be threaded while the head 124 has a smooth outer surface. The head 124 is configured to have a diameter slightly larger than the diameter of the central hole 110 of the crimp plate 102. Thus, when the head 124 is seated within the central hole 110, the deformable members 122 are pushed radially outward by the head 124, away from the longitudinal axis of the central hole 110 into the suture holes 118.

In another exemplary embodiment, the fixation element 104 includes only a head 124 without a shaft. Thus, the fixation element 104 of this embodiment is configured to crimp the suture in place without fixing the crimp plate 102 to the bone. The fixation element 104 preferably has a flat head 124 to allow the fixation element 104 to lie flush with the crimp plate 102 when inserted therein and into the target tissue to prevent irritation to the patient. In an exemplary embodiment, the head 124 has a smooth outer surface that enables easy positioning within the central hole. However, in another exemplary embodiment, the head 124 may include threading about an outer surface thereof.

The suture 106 employed with the crimp plate 102 extends from a first end 130 to a second end 132 and may be formed as a regular suture, braids, tapes, suture chains, suture tapes, sutures with collagen, or combinations thereof. In an exemplary embodiment, the suture 106 is a woven polyester suture made from PET (polyetheylene terephthalate), the same polyester as most commercially available sutures. The suture 106 may be poly-coated or uncoated. Those skilled in the art will understand that the suture 106 may be of any necessary length. The suture 106 has a width greater than the width of the slots 120, as described above, so that the suture 106, when threaded through the suture holes 118, is unable to pass through the slot 120 into the central hole 110. In an exemplary embodiment, the suture 106 may include an anchor or enlarged element at one end to prevent the end from passing through the suture hole 118 as the suture 106 is passed around the target bone(s). It is noted that although the present embodiments describe the use of only a single suture, the present disclosure also contemplates the use of multiple sutures in the reduction of the syndesmosis.

Figure 4:
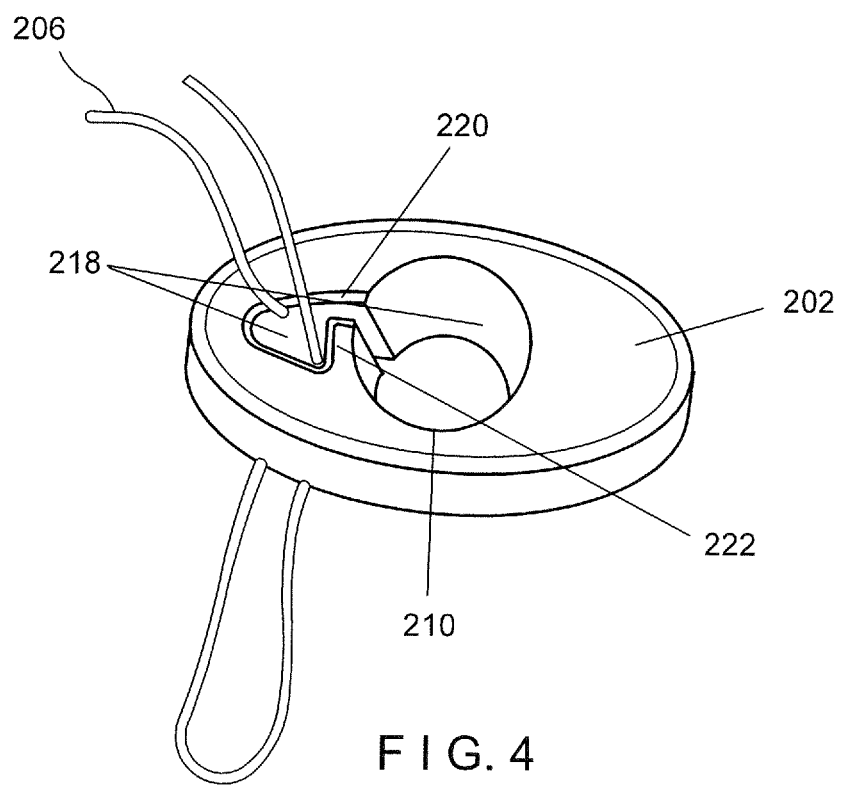
FIG. 4 shows a perspective view of a crimp plate according to another exemplary embodiment of the present disclosure.

FIG. 4 depicts a crimp plate 202, according to another exemplary embodiment of the present disclosure, that is substantially similar to implant system 100, except as described herein. Specifically, crimp plate 202 includes a central hole 210 but only a single suture hole 218. The suture hole 218 is substantially the same size and shape as the suture holes 118 and is open to the central hole 210 via a slot 220. The slot 220, suture hole 218, and central hole 210 form a deformable member 222 therebetween, similar to deformable member 122, that deflects into the suture hole 218 when a fixation member is inserted into the central hole 210. However, in this embodiment, instead of the suture 106 being passed through two suture holes, the suture 106 is passed through the suture hole 218 twice such that two portions of the suture 206 are crimped within the single suture hole 218, as shown in FIG. 4.

In an exemplary method according to the present disclosure, the implant system 100 is delivered to the target tissue using known techniques. For example, an incision is made over the outside of the ankle so that the fibula and syndesmosis may be identified and exposed. The fibula and tibia are reduced by tensioning the fibula toward the tibia. After appropriate reduction of the tibia and fibula, in one embodiment, the suture 106 is wrapped around the bones. However, it will be understood that the suture 106 may be passed through a hole/tunnel in the fibula (or other bone) and thereafter fixed to the tibia (or other bone). In this embodiment, the first end 132 of the suture 106 is be pre-threaded through a first one of the suture holes 118 of the crimp plate 102 prior to passing the suture 106 around the bones. However, in another exemplary embodiment, the crimp plate 102 is be threaded over both ends 130, 132 of the suture 106 after the suture 106 has been positioned about the bones. In an embodiment, the second end 132 of the suture 106 includes an anchor to prevent the second end 132 from passing through the suture hole 118 while the first end 130 is being positioned around the bones. Once the suture 106 has been positioned around the tibia and fibula, the first end 130 of the suture 106 is passed through the second suture hole 118 from a bone-facing side of the crimp plate 102 to the opposing side. Tension is then applied to the suture 106 (e.g., by hand) and the crimp plate 102 is slid along the suture 106 to a position adjacent the surface of the tibia. It is noted that, with the suture holes 118 on the outside of the screw hole 110, while tensioning the suture 106, the suture 106 will naturally be pulled to the outer edges of the suture holes 118, away from the central longitudinal axis L of crimp plate 102. To lock the crimp plate 102 and suture 106 in place, the fixation member 104 is inserted through the central hole 110 until the head 124 of the fixation member 104 lies flush with the outer surface 112 of the crimp plate 102, deflecting the deformable members 118 radially outward away from the central longitudinal axis L of the crimp plate 102 and into the suture holes 118. The deflected deformable members 118 push the suture 106 against the walls of the suture holes 118, crimping the suture 106 and locking it in the desired position (i.e., at the desired tension). In an exemplary embodiment, the fixation member 104 is a screw with a head 124 and a shaft 126. In this embodiment, the screw shaft may be inserted into a pre-drilled hole within the tibia or screwed straight into the bone as would be understood by those skilled in the art. However, it will be understood that, in another embodiment, the fixation member 104 may only include a head 124. In this embodiment, the fixation member 104 crimps the suture 106 in place within the crimp plate 102 without fixing the crimp plate 102 to the bone.

In some situations it may be preferable to temporarily fix the suture 106 in place within the crimp plate 102 with enough friction to maintain the reduction in the bone while checking the positioning of, for example, the suture 106 or the crimp plate 102. In this case, the fixation member 104 may be inserted only partially through the central hole 110 such that the deformable members 122 are deflected outwardly enough to crimp the suture 106 in place within the suture holes 118 without being permanently deformed. If necessary, the fixation member 104 may be removed from the central hole 110, releasing the deformable members 122 so that they move back toward the central longitudinal axis L of the crimp plate 102, allowing the suture 106 to move freely through the suture holes 118. The crimp plate 102 and suture 106 may then be repositioned as necessary and the fixation member 104 again inserted through the central hole 110 to again temporarily or permanently crimp the suture 106 in place.

It will be understood that although the present embodiments relate to use of the system 100 for an ankle syndesmosis, the system 100 is not limited to use within the ankle. Rather, the system 100 may be used in various other procedures anywhere within the body such as, for example, AC joint repair and applications in the foot to correct deformities.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiments disclosed, but rather modifications are also covered within the scope of the present invention as defined by the appended claims.

What is claimed is:

1. A suture crimp plate, comprising:
   a body including a first bone-facing surface and a second opposing surface;
   a central hole extending through the body from the first surface to the second surface and sized and shaped to receive a bone fixation device; and
   a first suture hole extending through the body from the first surface to the second surface and sized and shaped to receive a suture therethrough, the first suture hole being open to the central hole via a first slot, a first deformable member being formed between the first suture hole and the central hole,
   wherein, when a bone fixation element is inserted into the central hole, the first deformable member is configured to be deflected away from a central longitudinal axis of the central hole and into the first suture hole to clamp the suture therein relative to the crimp plate.

2. The plate of claim 1, further comprising:
   a second suture hole extending through the body from the first surface to the second surface and sized and shaped to receive a suture therethrough, the second suture hole being open to the central hole via a second slot, a second deformable member being formed between the second suture hole and the central hole, wherein the second deformable member is movable away from a central longitudinal axis of the central hole and into the second suture hole to clamp the suture therein relative to the crimp plate.

3. The plate of claim 2, wherein the first and second suture holes have a triangular profile.

4. The plate of claim 2, wherein the first and second suture holes are positioned on opposing sides of the central hole.

5. The plate of claim 1, wherein the first deformable member is formed of a shape-memory material.

6. The plate of claim 1, wherein the central hole tapers in diameter from the first surface to the second surface.

7. The plate of claim 1, wherein the central hole includes threading configured to mate with threading on an outer surface of the bone fixation element.

8. An implant system, comprising:
   a crimp plate including:
      a body including a first bone-facing surface and a second opposing surface;
      a central hole extending through the body from the first surface to the second surface and sized and shaped to receive a bone fixation device; and
      a first suture hole extending through the body from the first surface to the second surface and sized and shaped to receive a suture therethrough, the first suture hole being open to the central hole via a first slot, a first deformable member being formed between the first suture hole and the central hole;
   a bone fixation element configured to be inserted through the central hole such that, when the bone fixation element is inserted through the central hole, the first deformable member is deflected away from a central longitudinal axis of the central hole and into the first suture hole to clamp the suture therein relative to the crimp plate; and
   at least one suture configured to be passed through the first suture hole.

9. The system of claim 8, wherein the crimp plate further includes a second suture hole extending through the body from the first surface to the second surface and sized and shaped to receive a suture therethrough, the second suture hole being open to the central hole via a second slot, a second deformable member being formed between the second suture hole and the central hole, wherein the second deformable member is movable away from a central longitudinal axis of the central hole and into the second suture hole to clamp the suture therein relative to the crimp plate.

10. The system of claim 9, wherein the first and second suture holes are positioned on opposing sides of the central hole.

11. The system of claim 8, wherein the bone fixation element includes a head and a shaft, a diameter of the head being larger than a diameter of the central hole.

12. The system of claim 8, wherein the bone fixation element includes only a head, a diameter of the head being larger than a diameter of the central hole.

13. The system of claim 8, wherein the central hole tapers in diameter from the first surface to the second surface.

14. The system of claim 8, wherein the first deformable member is formed of a shape-memory material.

15. The system of claim 8, wherein the at least one suture includes an anchor at a first end thereof, the anchor preventing a second end of the suture from passing through the suture hole when the suture is passed therethrough.

16. A method for treating a fracture, comprising:
    positioning a suture about a target bone, a first end of the suture being pre-threaded through a first suture hole of a crimp plate, the crimp plate comprising:
        a body including a first bone-facing surface and a second opposing surface;
        a central hole extending through the body from the first surface to the second surface and sized and shaped to receive a bone fixation device; and
        first and second suture holes extending through the body from the first surface to the second surface and sized and shaped to receive a suture therethrough, the first and second suture holes being open to the central hole via a first and second slots, respectively, a first deformable member being formed between the first suture hole and the central hole and a second deformable member being formed between the second suture hole and the central hole;
    passing a second end of the suture through the second suture hole of the crimp plate;
    sliding the crimp plate along the suture to a position adjacent the target bone; and
    inserting a bone fixation member through the central hole such that the first and second deformable members are deflected away from a central longitudinal axis of the central hole and into the first and second suture holes to clamp the suture therein relative to the crimp plate.

17. The method of claim 16, further comprising:
    applying tension to the suture by hand to facilitate sliding of the crimp plate therealong.

18. The method of claim 16, wherein the first and second deformable members are formed of a shape-memory material.

19. The method of claim 18, further comprising:
    inserting the bone fixation member only partially through the central hole such that the deformable members are deflected outwardly enough to crimp the suture in place within the first and second suture holes without being permanently deformed; and
    repositioning the crimp plate along the target bone.

20. The method of claim 16, wherein the first and second suture holes are positioned on opposing sides of the central hole.

\* \* \* \* \*